United States Patent [19]

Wu

[11] Patent Number: 4,671,788
[45] Date of Patent: Jun. 9, 1987

[54] MOXIBUSTION DEVICE WITH MOVEABLE MOXA CHAMBER

[76] Inventor: Shuenn J. Wu, No. 18, Alley 1, Lane 716, Lih Ren Road, Tainan City, Taiwan

[21] Appl. No.: 878,354

[22] Filed: Jun. 25, 1986

[51] Int. Cl.$^4$ .................. A61M 37/00; A61F 7/00
[52] U.S. Cl. ..................... 604/24; 604/291; 128/399
[58] Field of Search ............ 604/24, 113, 310–315, 604/291; 128/399, 402, 403; 248/206.3, 363

[56] References Cited

U.S. PATENT DOCUMENTS

| | | | |
|---|---|---|---|
| 1,817,823 | 8/1931 | Ito | 604/24 |
| 2,580,169 | 12/1951 | Golden et al. | 604/311 |
| 4,090,517 | 5/1978 | Takenaka | 128/399 |
| 4,203,438 | 5/1980 | Shiu | 604/24 |
| 4,604,088 | 8/1986 | Nottbohm | 604/24 |

*Primary Examiner*—C. Fred Rosenbaum
*Assistant Examiner*—J. L. Kruter
*Attorney, Agent, or Firm*—Morton J. Rosenberg

[57] ABSTRACT

A device for burning, utilizing and enhancing the therapeutic effect of moxa, comprising a cover, a base and a moxa container. The cover is shaped like an upside-down bowl with an opening on its top center. The cover is disposed on the base and has an opening on its top to receive and engage with the moxa container. The base has three legs which stabilize the moxibustion device on human body. The container has a plunger which has an enlarged end and a head to press the moxa contained therewithin together so as to increase its therapeutic effectiveness.

11 Claims, 5 Drawing Figures

MOXIBUSTION DEVICE WITH MOVEABLE MOXA CHAMBER

BACKGROUND OF THE INVENTION

Acupuncture and moxibustion are important and powerful therapeutics in traditional Chinese medicine. Acupuncture is now famous throughout the world and is being developed and researched by modern western medicine. This has resulted in many new developments, such as the replacing of traditional needles with laser beams.

Moxibustion, however, as of yet has not been highly respected by modern medicine. Traditional moxibustion, although medically effective, is therapeutically crude and rough. And actually, it has been inconvenient, troublesome and limited to on specific areas of the human body. This may be the reason that the moxibustion has not yet been used worldwide and has not been applied in modern medicine.

SUMMARY

It is a primary object of the present invention to provide a moxibustion device which can be fed moxa directly and easily without any interruption of therapy.

It is another object of the present invention to provide a moxibustion device which has a moxa container to increase therapeutical effectiveness, reduce the therapeutical period, decrease the number of additions of moxa, extend the effective period of a certain amount of moxa and save time.

It is a further object of the present invention to provide a moxibustion device which uses a plunger to press the moxa together to maintain the temperature for therapy.

It is a further object of the present invention to provide a moxibustion device wherein the distance between the burning moxa and the skin of the patient is adjustable.

It is a further object of the present invention to provide a moxibustion device which is easy, safe and convenient to use.

DETAILED DESCRIPTION OF THE PREFERRED EMBODIMENT

Figure 1:
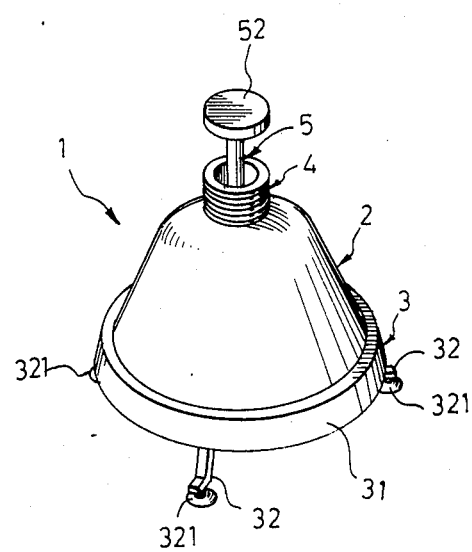
FIG. 1 is a perspective view of the preferred embodiment in accordance with the invention.
Figure 2:
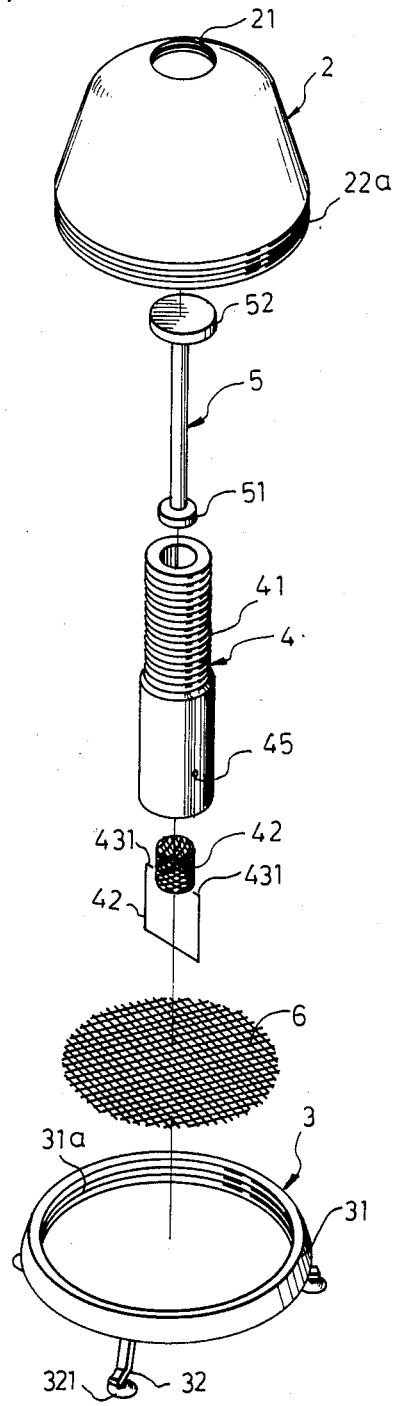
FIG. 2 is a fragmental view of the preferred embodiment in accordance with the invention as shown in FIG. 1.
Figure 3:
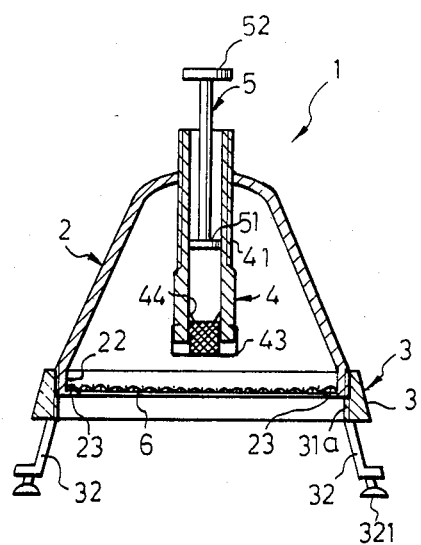
FIG. 3 is a cross-sectional view of the preferred embodiment in accordance with the invention as shown in FIG. 1.

Referring to the drawings, and in particular to FIGS. 1, 2 and 3, it can be seen that the moxibustion device 1 of the present invention comprises a cover 2, a base 3 and a moxa container 4.

The cover 2 is an upside-down bowl-like member which has a threaded opening 21 on its top center and a cylindrical portion 22 extending from the mouth of the bowl-like cover 2. An inward rim 23 is provided on the outmost position of the cylindrical portion 22 to support a netted moxa ash tray 6.

The base 3 is a hollow cylinder 31 with a plurality of legs 32, preferably three, disposed thereunder so as to stabilize the present invention on the surface of the patient (not shown). A suction cup 321 is disposed on the lowermost end of each leg 32 so as to secure the present invention on the patient's body. The outside surface of the cylindrical portion 22 of the cover 2 and the inner diameter of the hollow cylinder 31 of the base 3 are provided with threads (22a and 31a, respectively) which engage with each other so as to secure the cover 2 with the base 3 and so as to allow the distance between the cover 2 and human body (not shown) to be adjustable. The engaging means of the base is female threading and the engaging means of the cover is male threading.

The moxa container 4 is preferably a tube-like member, the outside surface of which has threads 41 transversing a suitable length. These threads 41 engage with threaded opening 21 of the cover 2 so as to allow for the adjustability of the relative distance between the tube-like moxa container 4 and the cover 2. The lower end of the moxa container 4 has a moxa net 42 on its inside which keeps the burning moxa therewithin. Further, a retainer 43 is provided on the lower end of the moxa container 4. This retainer 43 is affixed to the lower end of the moxa container 4 so as to prevent the moxa net 42 from dropping or being forced out thereof. The retainer 43 is a U-shaped resilient wire with a small inward projection 431 on each of the two legs of the U-shaped retainer 43. Disposed in close proximity with the lower end of the moxa container 4 are two apertures 45 which correspond to the projections 431 of the retainer 43. The projections 431 are insertable into the apertures 45, thus keeping the retainer 43 there and preventing the moxa net 42 from dropping out of the moxa container 4. Inside the moxa container 4, two opposite hooks 44, which are inclined downwardly, are disposed at a position approximately the height of the moxa net 42 from the lower end of the moxa container 4. This prevents the burning moxa from falling out of the moxa container 4 when the container 4 is placed upside down. After moxa is fed into the moxa container 4, a plunger 5 with an enlarged end 51 and a plunger head 52 is inserted into the tube-like moxa container 4. The surface area and the cross-sectional shape of the enlarged end 51 are almost the same as the inside cross-sectional area and shape of the moxa container 2. The plunger head 52 is bigger than the enlarged end 51, thus preventing the plunger 5 from dropping into the moxa container 4. The enlarged end 51 is inserted into the moxa container so as to lightly press the moxa together, thereby generating high density heat radiation from the burning moxa, thus increasing its medical effectiveness.

Figure 4:
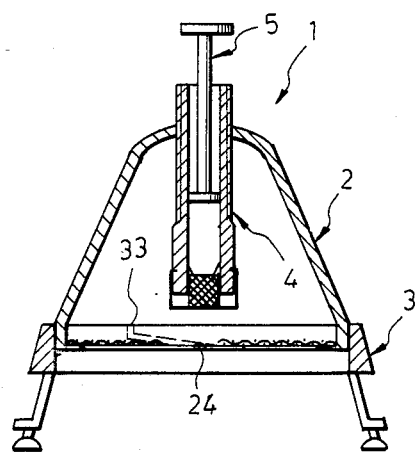
FIG. 4 is a second embodiment in accordance with the invention.

Although this invention has been described as a preferred embodiment, there are many other possible variations other than those hereinbefore set forth without departing from the spirit and essential characteristics of the invention. Examples of these variations can be seen in FIGS. 4 and 5. In FIG. 4, it can be seen that on the outside surface of the cylindrical portion 22 there are a plurality of small projections 24 (only one is shown), while there are a plurality of sloped slots 33 (only one is shown) provided on the inner diameter of the hollow cylinder 31 of the base 3 corresponding to the projections 24. By the engagements of the projections 24 with corresponding slots 33, the cover 2 is adjustably disposed on the base 3.

Figure 5:
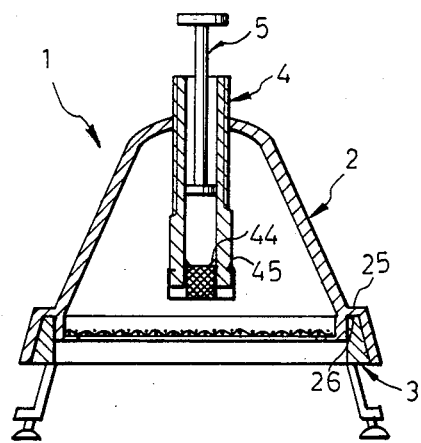
FIG. 5 is a third embodiment in accordance with the invention.

In FIG. 5, a third embodiment is shown, wherein a circumferential skirt 25 is formed integrally outside the cylindrical portion 22 of the cover 2, extending downwardly and defining a circumferential slot 26 with the outside surface of the cylindrical portion 22. The base 3 is then squeezed into the slot 26.

I claim:

1. A moxibustion device comprising:

a base which is constituted by a hollow base body and supporting means, said supporting means being disposed under said base body, said hollow base body having engaging means for engaging with and holding a cover;

said cover having a wide mouth corresponding to the inner diameter of said hollow base body and a threaded opening disposed on the top thereof for receiving a moxa container, said mouth further having an extended cylinder, said cylinder having engaging means for engagement with said engaging means of said hollow base body and an inner circumferential rim to support a netted moxa-ash tray;

a netted moxa-ash tray disposed on the inward rim of said cover preventing hot moxa-ash from dropping directly on human body;

a hollow moxa container having one end being provided with a moxa net disposed therein and retaining means to retain said moxa net, said moxa container further being provided with a threaded zone on the outside surface to engage with the threaded opening of said cover;

a plunger having an enlarged end corresponding to the inside shape of said moxa container, said plunger also having a plunger head which prevents said plunger from dropping into said moxa container.

2. A moxibustion device as set forth in claim 1, wherein said supporting means for said base is a plurality of legs.

3. A moxibustion device as set forth in claim 2, further comprising a suction cup disposed under and attached to each of said leg.

4. A moxibustion device as set forth in claim 1, wherein the retaining means is a U-shaped wire with two inward projections at the end of each leg thereof, said moxa container being provided with two apertures which are near the end where the moxa net is disposed therein and which correspond to the projections of the U-shaped retaining means in order to receive the projections of the retaining means.

5. A moxibustion device as set forth in claim 1, further comprising two opposite downwardly-inclined hooks which are disposed inside the moxa container at a position approximately the height of the moxa net from the end where the moxa is disposed therein.

6. A moxibustion device as set forth in claim 2, wherein the number of the legs is three.

7. A moxibustion device as set forth in claim 1, wherein said base body is a hollow cylinder.

8. A moxibustion device as set forth in claim 1, wherein said cover is an upside-down bowl-like member having said threaded opening at its top center.

9. A moxibustion device as set forth in claim 1, wherein said moxa container is a tube-like member.

10. A moxibustion device as set forth in claim 1, wherein the engaging means of said base is a female thread and the engaging means of said cover is a male thread.

11. A moxibustion device as set forth in claim 1, wherein the engaging means of said base is a plurality of sloped slots and the engaging means of said cover is a plurality of projections corresponding to said slots.

* * * * *